(12) United States Patent
Homann et al.

(10) Patent No.: US 9,186,285 B2
(45) Date of Patent: Nov. 17, 2015

(54) FOLDED INCONTINENCE ARTICLE

(75) Inventors: Vanessa Homann, Heidenheim (DE); Ruediger Kesselmeier, Herbrechtingen (DE)

(73) Assignee: PAUL HARTMANN AG, Heidenheim (DE)

( * ) Notice: Subject to any disclaimer, the term of this patent is extended or adjusted under 35 U.S.C. 154(b) by 203 days.

(21) Appl. No.: 13/988,977

(22) PCT Filed: Nov. 18, 2011

(86) PCT No.: PCT/EP2011/005831
§ 371 (c)(1),
(2), (4) Date: Jul. 24, 2013

(87) PCT Pub. No.: WO2012/069166
PCT Pub. Date: May 31, 2012

(65) Prior Publication Data
US 2014/0046286 A1 Feb. 13, 2014

(30) Foreign Application Priority Data
Nov. 23, 2010 (DE) .......................... 10 2010 052 264

(51) Int. Cl.
A61F 13/56 (2006.01)
A61F 13/58 (2006.01)
A61F 13/62 (2006.01)
A61F 13/15 (2006.01)
A61F 13/64 (2006.01)

(52) U.S. Cl.
CPC ............ *A61F 13/58* (2013.01); *A61F 13/15756* (2013.01); *A61F 13/5622* (2013.01); *A61F 13/64* (2013.01); *A61F 2013/15121* (2013.01)

(58) Field of Classification Search
CPC .................................. A61F 13/58; A61F 13/64
See application file for complete search history.

(56) References Cited

U.S. PATENT DOCUMENTS

| 2001/0034512 | A1 | 10/2001 | Karlsson et al. |
| 2001/0056271 | A1 | 12/2001 | Shingu et al. |
| 2002/0123730 | A1* | 9/2002 | Popp et al. ............... 604/385.03 |
| 2008/0097368 | A1 | 4/2008 | Molander |
| 2008/0208152 | A1 | 8/2008 | Eckstein et al. |
| 2008/0208156 | A1 | 8/2008 | LaVon et al. |
| 2009/0043275 | A1* | 2/2009 | Perneborn ..................... 604/391 |
| 2010/0010465 | A1* | 1/2010 | Winqvist et al. ............. 604/389 |
| 2010/0065199 | A1 | 3/2010 | Hormung et al. |
| 2010/0318055 | A1 | 12/2010 | Hormung et al. |
| 2011/0100526 | A1 | 5/2011 | Umebayashi |
| 2011/0146892 | A1 | 6/2011 | Ostertag |
| 2011/0301563 | A1* | 12/2011 | Maruhata et al. ............. 604/389 |

(Continued)

FOREIGN PATENT DOCUMENTS

| DE | 10 2004 021 353 A1 | 11/2005 |
| DE | 10 2005 035 544 A1 | 2/2007 |

(Continued)

OTHER PUBLICATIONS

International Search Report issued by the European Patent Office in International Application PCT/EP2011/005831.

*Primary Examiner* — Susan Su
(74) *Attorney, Agent, or Firm* — Henry M. Feiereisen LLC (57) ABSTRACT

The invention relates to an absorbent incontinence article of the open type having attached diaper wings, wherein the rear diaper wings have closure elements in the edge region, and to the folding of the diaper wings at high production speeds without impairing the functionality of the closure elements and simultaneously the user-friendly arrangement of the closure elements in the folded absorbent incontinence article. The invention also relates to a method for producing the absorbent incontinence article.

22 Claims, 4 Drawing Sheets

(56) References Cited

U.S. PATENT DOCUMENTS

2011/0303351 A1  12/2011  Nakakado
2014/0039443 A1* 2/2014  Nagai et al. .................... 604/389

FOREIGN PATENT DOCUMENTS

| | | |
|---|---|---|
| DE | 10 2006 050 971 A1 | 4/2008 |
| DE | 10 2007 024 180 A1 | 11/2008 |
| DE | 10 2008 046 358 A1 | 3/2010 |
| DE | 10 2009 022 529 A1 | 12/2010 |
| EP | 1 005 316 B1 | 9/2002 |
| EP | 1 166 735 B1 | 3/2007 |
| WO | WO 2005/110321 A1 | 11/2005 |
| WO | WO 2007/058761 A1 | 5/2007 |
| WO | WO 2010/032397 A1 | 3/2010 |
| WO | WO 2010/092935 A1 | 8/2010 |

* cited by examiner

FOLDED INCONTINENCE ARTICLE

CROSS-REFERENCES TO RELATED APPLICATIONS

This application is the U.S. National Stage of International Application No. PCT/EP2011/005831, filed Nov. 18, 2011, which designated the United States and has been published as International Publication No. WO 2012/069166 A1 and which claims the priority of German Patent Application, Serial No. 10 2010 052 264.3, filed Nov. 23, 2010, pursuant to 35 U.S.C. 119(a)-(d).

BACKGROUND OF THE INVENTION

The present invention relates to folded, absorbent incontinence articles of the open type for incontinent adults, and to a method for folding absorbent incontinence articles.

DE-102005035544-A1 already describes an incontinence article with material sections, often also referred to as diaper wings, attached to the lateral edges of the main part, said material sections having closing elements in the edge section, the diaper wings being folded onto themselves about at least two fold lines and turned in onto the side of the main part which faces the body, in order to form an arrangement turned in on itself which is detachably fastened at a first joining point.

EP-1005316-B1 describes the z-shaped folding of the diaper wings of a diaper of the open type, in which first the outer end of the wings is folded back by at least the width of the closing surface and subsequently folded back in this configuration toward the front by the double width of the closing surface, such that the closing elements in this folded configuration are not covered by any layer of material and are instantly visible to the user.

EP-1166735-B1 also describes a z-shaped or inverted z-shaped folding of the rear diaper wings, the first fold inward being onto the chassis of the diaper and the free end of the lateral part subsequently being folded outward once or multiple times in such a way that said free end faces outward in the folded state and is easily unfolded when applying the diaper—particularly to persons confined to a bed.

WO-2005/110321-A1 describes the folding of absorbent sanitary articles along first and second longitudinal fold lines such that the outer edges of the diaper wings project beyond the fold line such that the folded article is easy to unfold, since the outer edge having the closing elements is directly reachable.

WO-2007/058761-A1 describes the manufacture of absorbent sanitary articles with separately attached diaper wings at high machine speeds without the article or the closing elements being inadvertently crumpled or folded, by performing a folding which protects the diaper wings and the closing elements. For this purpose, the diaper wing, which has a closing element on its inward facing side in the applied state, is turned over about a longitudinal axis onto the inside of the chassis and subsequently the entire lateral part is turned over onto the chassis about a second longitudinal axis, the second fold width being at least as wide as the first, such that the first section turned inward is not once again folded by the second folding.

DE-102004021353-A1 discloses an absorbent incontinence article with a main part, consisting of a front section, a back section and a crotch section which lies in the longitudinal direction between the front and back sections and is intended to be placed between the legs of a user, the main part having an absorbent body, and with rear material sections attached to the back section and with front material sections attached to the front section, the rear and front material sections extending in the transverse direction beyond lateral longitudinal edges of the main part, the material sections having, in the applied state, on the side facing the body an inside and, in the applied state, on the side facing away from the body an outside, and the rear material sections having closing elements on an outer edge section of the rear material sections, the rear and front material sections connecting the front section and the back section to one another in the applied state of the article, and the material sections being folded onto themselves and inward onto the side of the back section of the main part facing the body prior to use of the folded-together article.

Based on this prior art, the problem with the folded incontinence articles is that the proportion of products not conforming to specifications increases at high production speeds in the manufacturing process. Not conforming to specifications refers to products which do not meet the requirements determined by the manufacturer with respect to the quality of the products. Product quality is compromised at increased production speeds in that the closing elements attached to the folded diaper wings are unintentionally opened during production. In the event that the incontinence article containing the folded diaper wings and the unintentionally opened closing elements is longitudinally and/or transversely folded in the next production step, the opened or partially opened closing element will come in contact with other material layers of the incontinence article and thus is unintentionally fastened on them. This leads to the incontinence article not being able to be unfolded in the usual manner and to the closing elements, in certain circumstances, no longer being usable according to an intended fastening method. If suchlike incontinence articles were not removed from the production process, the unintentional fastening would be further strengthened in the subsequent packing under pressure of the incontinence articles, such that products like these would become unusable, as they can no longer be properly opened and applied.

SUMMARY OF THE INVENTION

The object of the present invention is to produce absorbent incontinence articles of the open type with attached diaper wings at high production speeds without impairment of the functionality of the closing means. Moreover, the incontinence articles should be made available in a user-friendly arrangement.

This object is achieved according to the invention by an incontinence article of the open type with rear material sections attached to a lateral edge section in the back section of the main part, and with front material sections (diaper wings, lateral flaps or sections) attached in the front section, such that prior to use of the incontinence article the rear material sections, the edge section of which has a closing element which comprises a closing element tape with a free fingerlift tab which is folded back onto the inside of the material section prior to use, are folded onto themselves along fold lines extending parallel to the longitudinal direction and forming inner segments, central segments and outer segments, the inner segments being attached to the respective lateral edge section of the main part and the outer segments comprising the longitudinal edge section and the central segments being folded onto the inside of the outer segments in such a way that the central segments fully cover the free fingerlift tab of the closing element tape and that the thus folded rear material sections are turned in inward along turning-in axes onto the inside of the back section of the main part to form a turned-in arrangement, the inside of the edge section in the turned-in arrangement being oriented facing away from the inside of the back section of the main part.

For closing the incontinence article when applied, the closing element tapes interact adhesively detachably together with an outside of the front section of the main part and/or the material sections in the front section. For this purpose, the closing element tapes may have, for instance, a pressure-sensitive adhesive zone or mechanical closing aids, such as hooks and loops.

The inventors have realized that the cause of the unintentional opening of the closing element tapes in the production process is a draft force which bears on the closing element tapes and which increases with increasing production speeds. The risk of impact from this draft force is particularly present at the point in time when the rear material sections in the folded arrangement are already turned in onto the inside of the main part and, in particular, immediately prior to or during subsequent folding of the incontinence article transversely to its longitudinal direction. When this draft force exceeds the adhesive force of the closing element tape on the inside of the material section onto which it was turned back, the closing element opens unintentionally. As described above, suchlike incontinence articles are often completely unusable.

The inventors have further realized that the closing elements are protected to the greatest extent from the occurring draft force by the arrangement according to the invention. This will be explained in more detail with reference to the figures.

The inventors have, in a preferred embodiment of the incontinence article according to the invention, further provided a product which, as a result of the arrangement of the outer longitudinal edge sections of the rear material sections being such that these are oriented facing away from the longitudinal center axis of the product in the direction of the outer lateral longitudinal edges of the main part, can be comfortably unfolded by the user.

In order for the user to identify the rear material sections as being such and to be able to comfortably grip and unfold them, the closing element tape of the absorbent incontinence article is preferably covered over at least 25% and at most 90% of its extent in the transverse direction, preferably over at least 40% and at most 75% of its extent in the transverse direction, by central segments, or the central segments cover the closing element tape over at least 10 mm and at most 50 mm, furthermore preferably over at least 20 mm and at most 40 mm in the transverse direction.

Preferably, an outer lateral edge of the outer segment of a rear material section projects in the transverse direction beyond the central segments folded over said lateral edge by the dimension D.

The dimension D is preferably at least 10% and at most 85%, furthermore preferably at least 40% and at most 60%, of the width L5 of each outer segment. Alternatively, the projection in the transverse direction by the dimension D is preferably at least 5 mm and at most 50 mm, furthermore preferably at least 24 mm and at most 36 mm.

The rear material sections are preferably folded onto themselves such that they are divided by the folds into four segments each, the widths L3, L4 of the respective central segments being smaller than the widths L5 of the respective outer segments. Furthermore preferably, the widths L3, L4 of the central segments are identical, and/or the ratio of the widths L3, L4 of the central segments to the widths L5 of the outer segments is between 1:1 and 1:2.5.

The folding sequence of the rear material sections onto themselves is preferably such that first an outside of a respective rear material section is folded onto an outside, i.e. onto itself. The double-layered arrangement thus formed is subsequently once again folded onto itself, such that an inside of a respective rear material section is folded onto an inside. A regionally four-layered arrangement is formed. This may, if appropriate, be once again folded onto itself into an eight-layered arrangement. In the folding of the rear material sections onto themselves, fold lines preferably do not cut across the closing element tapes folded back on the inside of the material sections.

The rear material sections thus folded onto one another are preferably detachably fastened in the folded configuration, in particular by means of spot-like joining points created by ultrasonic welding. In the context of the detachable fastening of the folded material sections, reference is made to DE102009022529.3.

It is furthermore advantageous if a gripping region is provided on a respective longitudinal edge section of each of the folded rear material sections. This region intended for the manual gripping of the folded material section may comprise the entire longitudinal edge section. Preferably, the gripping region comprises a part of the longitudinal edge section which is free from joining points, preferably a region located in the center of the longitudinal edge section. It has been demonstrated that the detachable fastening by means of joining points may be designed such that the respective material section can be completely unfolded by a single tug on the corresponding gripping region, with preferably all of the joining points being released or coming apart.

In a development of the invention it is advantageous if the rear material sections have a surface extent (in cm$^2$) which is larger, preferably by at least 10%, in particular by at least 15%, than the front material sections. In particular, the length L7 of the rear material sections, that is to say their extent in the longitudinal direction of the diaper, may be at least 13 cm, furthermore in particular at least 18 cm, and furthermore in particular at least 22 cm. It is furthermore advantageous if the length L7 of the rear material sections is at least 10%, in particular at least 15%, furthermore in particular at least 20% and furthermore in particular at least 22% of the overall length of the disposable incontinence diaper. Advantageously, the overall length of the disposable incontinence diaper is 50-120 cm, in particular 60-110 cm and furthermore in particular 70-110 cm. It is furthermore advantageous if the front material sections have a length L6 which is, in particular at least 5%, furthermore in particular at least 10%, furthermore in particular at least 15% and furthermore in particular at most 50% shorter than the rear material sections. In a development of the invention it is advantageous if the width L1 of the material sections, that is the extent of the material sections in the transverse direction beyond the lateral edge of the main part of the diaper, is 12-40 cm, in particular 13-30 cm, furthermore in particular 14-27 cm. Preferably, the front material sections have the same width as the rear material sections.

Preferably, the front material sections are also folded onto themselves prior to use of the folded-together article, preferably along fold lines extending parallel to the longitudinal direction. The fold lines in such an instance divide the front material sections into four segments each, the widths L3, L4 of the central segments being smaller than the width L5 of the outer segments. Preferably, the folding of the front material sections onto themselves is such that first an outside of a respective front material section is folded onto an outside, i.e. onto itself. The double-layered arrangement thus formed is subsequently once again folded onto itself, such that an inside of a respective front material section is folded onto an inside.

It has furthermore proven advantageous if the front and/or rear material sections are made from a non-woven material. In particular, all non-woven materials which contain at least one component on the basis of a thermoplastic polymer in their composition are suitable. The non-woven materials may contain fibers of PE, PP, PET, rayon, cellulose, PA and blends of these fibers. Bi-component and multi-component fibers are also conceivable and advantageous. In particular, card webs, spun-bonded non-wovens, hydroentangled non-wovens, SM non-wovens, SMS non-wovens, SMMS non-wovens or also laminates made from one or multiple layers of these types of non-wovens are advantageous, wherein S refers to spunbond and M refers to meltblown non-woven layers. Spun-bonded non-wovens are particularly preferred, as these have a high strength in the longitudinal and transverse directions and thus can withstand particularly well the shearing forces bearing on them from any mechanical closing aids that may be used. In order to prevent fibers from being torn out of the non-woven structure in the process of releasing the mechanical closing aids, it is advantageous to provide the non-woven component with an embossed pattern, by means of which preferably all fibers of the non-woven component are integrated. In such an instance, a thermally embossed pattern is advantageous in particular, this being advantageously created in particular by calendering the non-woven with the addition of thermal energy.

For the manufacture of a folded incontinence article according to the invention, the rear material sections folded onto themselves are turned in along turning-in axes preferably extending through the main part of the diaper, preferably parallel to the longitudinal axis, onto the inside of the back section in such a way that the material sections come to lie at a small distance from one another or abut one another or overlap one another at least regionally. Advantageously, the lateral edge of the main part in the region of the attachment of the rear material sections could form the turning-in axes.

Accordingly, the invention also relates to a method for manufacturing a folded incontinence article as described above, the rear material sections first being folded onto themselves parallel to the longitudinal axis and the thus formed double-layered arrangement subsequently once again being folded onto itself parallel to the longitudinal axis, the free fingerlift tab of the closing element tape being fully covered by central segments to form an at least regionally four-layered arrangement. The rear material sections thus folded onto themselves are turned in inward along the turning-in axes onto the inside of the back section of the main part, such that the inside of the longitudinal edge section of a respective rear material section is oriented facing away from the inside of the back section of the main part.

Preferably, the material sections are first folded onto themselves, then fastened in a folded configuration to a first and a second lateral edge section on the back section of the main part and then turned in onto the inside of the main part.

In a development of this inventive idea, the incontinence article is folded inward onto itself at least once, preferably twice, preferably along fold lines extending in the transverse direction, preferably in such a way that the front section is first folded inward onto the inside of the main part and subsequently the back section is folded onto the front section. In this way, a product which is easily manageable in the manufacturing and packaging process due to its compact size is created, the visible sides of which being formed in the folded configuration by the material layer which also forms the outermost layer in the applied state, thus protecting the inside of the article from soiling prior to use.

Preferably the conveyance of the incontinence articles during manufacturing in a production machine, in particular subsequent to the method step of folding and turning in the rear material sections-along the turning-in axes inward onto the side of the back section of the main part which faces the body, is performed parallel to the longitudinal direction and at a web speed of more than 200 m/min, in particular more than 250 m/min, furthermore in particular more than 300 m/min, furthermore in particular more than 350 m/min. Preferably, the incontinence articles up to and including this aforementioned method step, are conveyed in a continuous state, that is to say with their respective later hip opening edges still connected to one another. It is preferably only in a downstream method step that the incontinence articles are separated from one another in the transverse direction to create the individual incontinence articles, and subsequently folded onto themselves as described earlier along fold lines extending in the transverse direction.

BRIEF DESCRIPTION OF THE DRAWING

Further features, details and advantages of the invention result from the attached patent claims, the drawings and the following description of a preferred embodiment of the invention. In the drawing

DETAILED DESCRIPTION OF PREFERRED EMBODIMENTS

Figure 1:
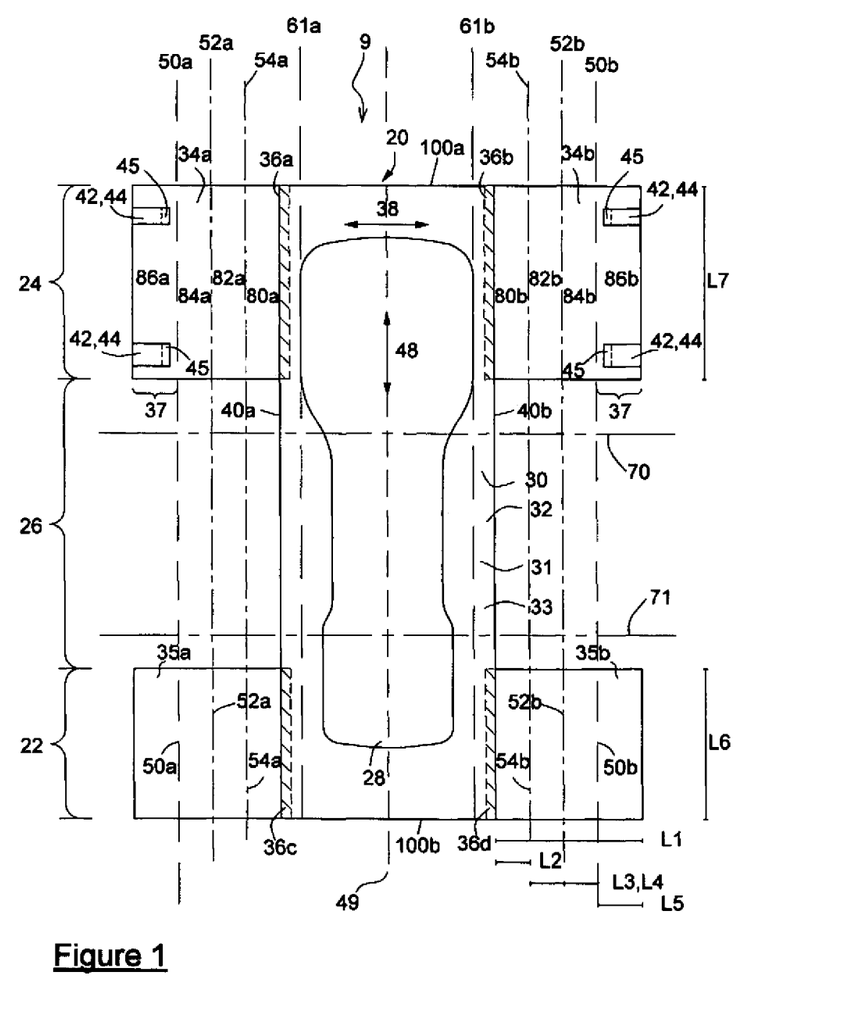
FIG. 1 is a plan view of a completely unfolded incontinence article
Figure 2:
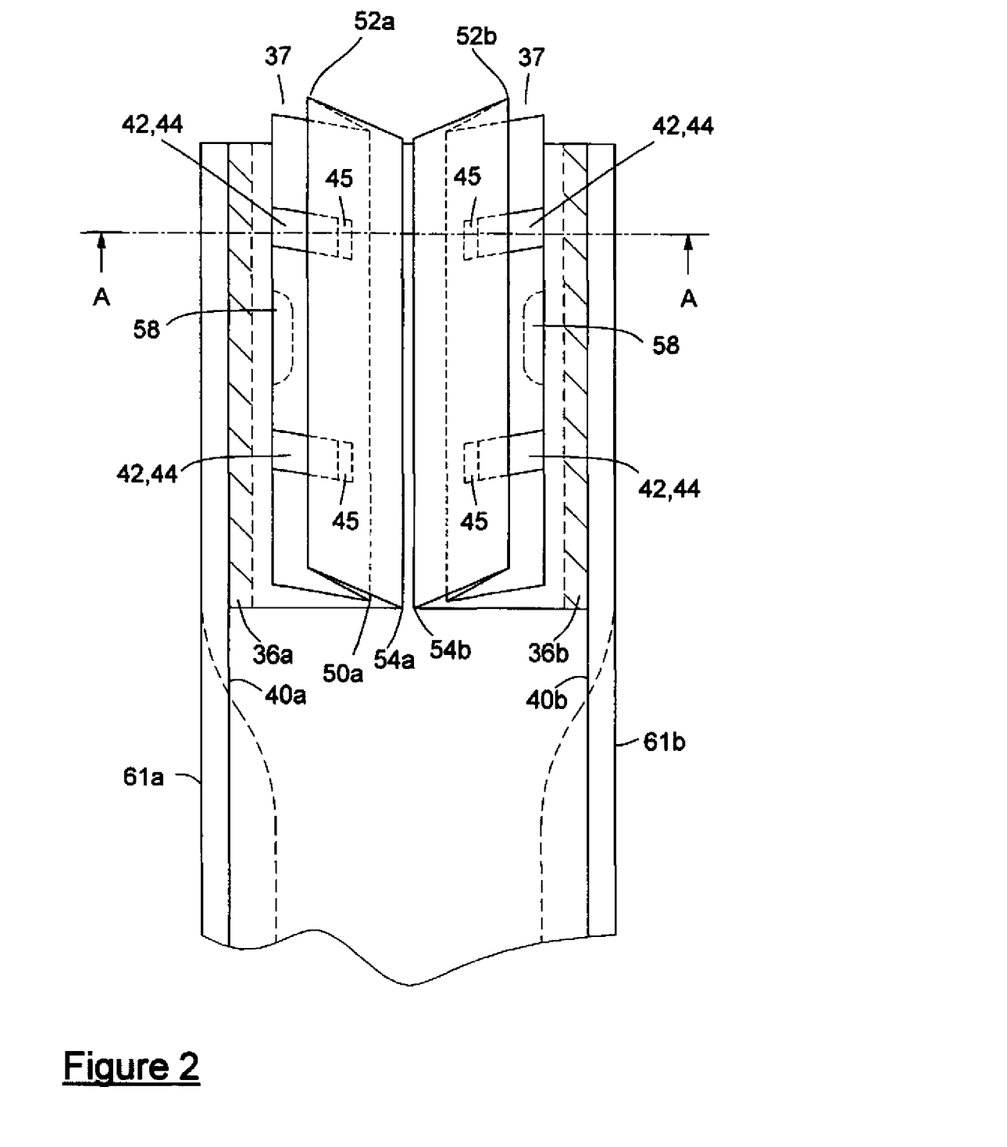
FIG. 2 is a partial plan view of an incontinence article folded according to the invention with rear material sections folded onto themselves
Figure 2A:
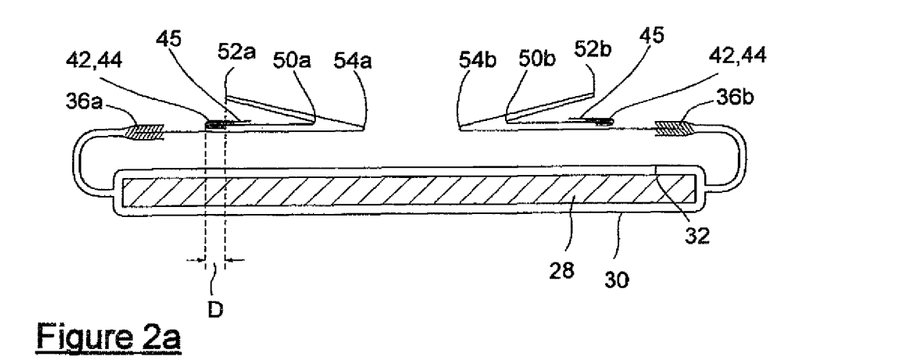
FIG. 2a is a sectional view of the incontinence article according to FIG. 2 (A-A)

An incontinence article 9 according to the invention is schematically shown in FIGS. 1, 2, and 2a. It comprises a main part, which is also often described as the chassis, which is referred to as a whole by the reference sign 20. The main part 20 comprises a front section 22, a back section 24 and a crotch section 26 which lies between the front and back sections and is intended to be placed between the legs of a user when the incontinence article 9 is applied to a user. The main part 20 comprises an absorbent body 28 which is suitably dimensioned for the absorption and permanent storage of bodily fluids. The absorbent body preferably comprises cellulose fibers and superabsorbent polymer particles (SAP) and is underpinned by a liquid-impermeable layer 30, which may also form the outer visible side of the incontinence article 9. A liquid-permeable topsheet 32 may be provided above the absorbent body 28.

In the back section 24, a first material section 34a forming a rear lateral flap or lateral section is overlappingly attached to a first lateral edge section 36a of the main part 20, and a second material section 34b forming a rear lateral flap or lateral section is overlappingly attached to a second lateral edge section 36b of the main part 20 (hatched areas in FIG. 1). The material sections 34a, 34b have a rectangular contour. Material sections 34a, 34b having a contouring at the leg cut-out would also be conceivable and advantageous, as disclosed in DE-102007024180-A1. The outer transverse edges of main part 20 and the rear material sections 34a, 34b form the rear hip opening edge 100a.

The side of the incontinence article 9 facing away from the body of the wearer in the applied state is described as the outside 31, the side of the incontinence article 9 facing toward the body of the wearer in the applied state is described as the inside 33. Based on this understanding, each component of the incontinence article 9 is to be assigned an inside and an outside in the just unfolded configuration of the incontinence article 9.

FIG. 1 shows a view of the inside 33 of the incontinence article 9 in its fully unfolded state. The rear material sections 34a, 34b each have two closing elements 42 with closing element tapes 44 which are folded onto themselves and unfoldable for their intended use and have free fingerlift tabs 45. It would also be conceivable to provide the rear material sections 34a, 34b with only one closing element 42 each. For closing the incontinence article in use, the closing element tapes 44 interact adhesively detachably with an outside 31 of the front section 22 of the main part 20 and/or the material sections in the front section 22. For this purpose, the closing element tapes may have a pressure-sensitive adhesive zone or a zone with mechanical closing aids, such as hooks and loops.

Material sections 35a, 35b also folded onto themselves and forming lateral sections, but not having any closing elements, are provided in the front section 22 of the incontinence article. The front material sections 35a, 35b have a rectangular contour. Material sections 35a, 35b having a contouring at the leg cut-out would also be conceivable and advantageous, as disclosed in DE-102007024180-A1. The outer transverse edges of main part 20 and the front material sections 35a, 35b form the front hip opening edge 100b.

The respective rear material section 34a, 34b is folded onto itself in the back section 24 of the main part, as shown in FIG. 2, in such a way that the central segments 82a, 84a, 82b, 84b fully cover the free fingerlift tab 45 of a respective closing element tape 44, and the arrangement of the outer longitudinal edge sections 37 of the rear material sections is such that these are oriented facing away from the longitudinal center axis of the product 49 in the direction of the outer lateral longitudinal edges 40 of the main part.

In the course of producing articles the incontinence articles 9, the respective rear material sections 34a, 34b, starting with the illustration in FIG. 1 and after having been folded on themselves, are folded inward along respective turning-in axes 61a, 61b which are parallel to the longitudinal direction 48 and extend within the main part 20 in the illustrated embodiment, into the position illustrated in FIG. 2 to form a turned-in arrangement. In this arrangement, the incontinence articles 9 are conveyed in the course of production, in particular in a continuous state, in the longitudinal direction at a high web speed, in particular at a web speed of more than 200 m/min, furthermore in particular at a web speed of more than 300 m/min, furthermore in particular at a web speed of more than 350 m/min. In such an instance, a strong draft ("airflow produced by motion") bears on the top side of the web. This causes the risk of a strong draft force bearing on the components which form the top side of the web.

Figure 3A:
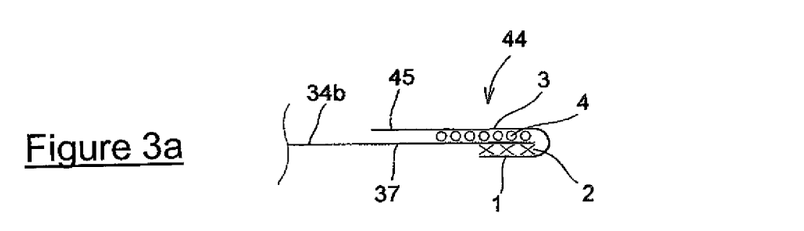
FIGS. 3a and 3b show sectional views of a closing element attached to the edge section of a rear material section
Figure 3B:
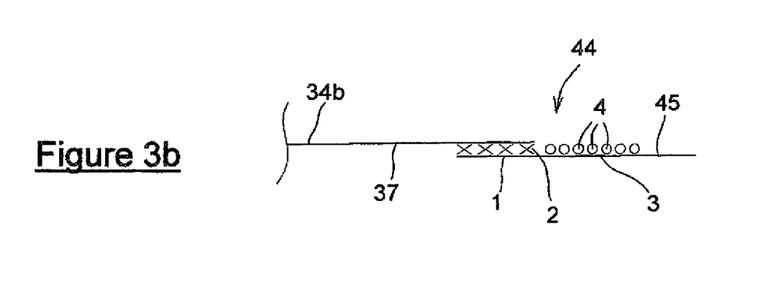

The inventors have realized that the closing element tapes are to a particular extent exposed to the risk of the influence of strong draft forces leading to production defects: At its manufacturer's end 1, the closing element tape 44 is usually inseparably, that is to say very firmly fastened, preferably by means of a permanent adhesive 2 or also by means of thermobonding or ultrasonic welding or other means of joining, to an edge section 37 of the rear material sections 34a, 34b (FIG. 3a). At its user end 3, however, the closing element tape 44 is usually fastened detachably in a non-destructive way for the purpose of later use, that is to say unfoldable into its used state by the user with little force, preferably by means of a pressure-sensitive adhesive 4 and/or mechanical closing elements such as hooks and loops. FIG. 3b shows the closing element tape 44 unfolded as intended immediately prior to use of the incontinence article, after having been detached from the inside 33 of the edge section 37 of a rear material section 34a, 34b. Moreover, the closing element 44 has a so-called fingerlift tap 45 at an outermost region of its user end 3, that is to say an end section which, for the purpose of easy gripping, by the user, can be detached by even less force or, preferably, as in the case illustrated, remains entirely unfastened.

In the arrangement according to the invention it is ensured that the fingerlift tab 45 is fully covered by the central segments 82a, 84a, 82b, 84b and that it is thus not part of the components which form the top side of the web and is thus not, or not as severely, exposed to the draft forces described above.

Preferably, in addition to the fully covered fingerlift tab 45, the closing element tape 44 is covered over at least 25% and at most 90% of its extent in the transverse direction 38, preferably over at least 40% and at most 75% of its extent in the transverse direction 38 by central segments 82a, 84a, 82b, 84b. Alternatively, the central segments 82a, 84a, 82b, 84b cover the closing element tape 44 over at least 10 mm and at most 50 mm, furthermore preferably over at least 20 mm and at most 40 mm in the transverse direction 38. This, on the one hand, ensures a high level of process reliability by means of preventing that an insufficient coverage of the closing element tape 44 by the central segments 82a, 84a, 82b, 84b leads to the draft force bearing on the covered material layers, potentially dislocating them, and in the process potentially exposing the fingerlift tab 45. On the other hand, the closing element 42 is readily identifiable by the user in this configuration, and the material sections can be comfortably gripped and unfolded.

In this context, it is advantageous if a gripping region 58 is provided on a respective edge section 37 of each of the rear material sections 34a, 34b (FIG. 2). The gripping region 58 is the region suitable for manually gripping the folded material section 34a, 34b for the purpose of unfolding it. The respective gripping region 58 of the material sections 34a, 34b in the configuration shown in FIG. 2 faces outward with reference to a longitudinal center axis of the product 49 of the incontinence article 9. By means of simultaneously gripping the gripping regions 58 with both hands and a tugging motion by both hands directed outward, the user can comfortably unfold the folded product. In such a case, in particular, there is no longer the necessity to first unfold the folded material sections 34a, 34b along the turning-in axes 61a, 61b prior to being able to unfold the folded material sections 34a, 34b with an outwardly directed tugging motion.

Furthermore preferably a respective rear material section 34a, 35a is folded in such a way that an outer lateral edge 11 of the outer segment 86a, 86b of a rear material section 34a, 34b projects in the transverse direction 38 beyond the central segments 82a, 84a, 82b, 84b folded over said lateral edge by the dimension D. The dimension D is preferably at least 10% and at most 85%, furthermore preferably at least 40% and at most 60% of the width L5 of each outer segment 86a, 86b. Alternatively, the projection in the transverse direction 38 by the dimension D is preferably at least 5 mm and at most 50 mm, furthermore preferably at least 24 mm and at most 36 mm.

The segments 80a, 82a, 84a, 86a of the material section 34a folded onto one another and the segments 80b, 82b, 84b, 86b of the material section 34b folded onto one another are preferably detachably fastened in the folded configuration, in particular by means of spot-like joining points created by ultrasonic welding, preferably with a diameter of 0.35 mm and an area of 0.0962 mm2. It has been demonstrated that this detachable fastening may be designed such that the respective material section 34a, 34b can be completely unfolded by a single tug on the respective first gripping region 58, with preferably all of the joining points being released or coming apart.

In the illustrated preferred embodiment, the rear material sections 34a, 34b, which are folded onto themselves in the longitudinal direction, are turned in onto the inside of the back section 24 along the turning-in axes 61a, 61b in such a way that the material sections 34a, 34b come to abut one another or to lie at a small distance from one another, but in any case do not overlap one another (FIG. 2a).

In an alternative embodiment it is, however, conceivable and advantageous to turn in the rear material sections 34a, 34b, which are folded onto themselves in the longitudinal direction, onto the inside of the back section 24 along the turning-in axes 61a, 61b to an extent that the material sections 34a, 34b come to lie overlapping one another at least regionally.

After completion of the longitudinal folding of the rear and front material sections and the turning in of the folded material sections onto the inside of the main part, the incontinence article 9 is preferably folded inward onto itself at least once, preferably twice, preferably along fold lines 70, 71 (FIG. 1) extending in the transverse direction 38, preferably in such a way that the front section 22 is first folded inward onto the inside 33 of the main part 20, and subsequently the back section 24 is folded onto the front section 22. In this way, a product which is easily manageable in the manufacturing and packaging process due to its compact size is created, the visible sides of which being formed in the folded configuration by the material layer 30, which also forms the outer layer in the applied state, thus protecting the inside 33 of the article 9 from soiling prior to use.

The dimensions of the segments 80b, 82b, 84b, 86b of the material section 34b in the illustrated embodiment are demonstrated with reference to FIG. 1. The dimensions are preferably identical to the dimensions of the segments 80a, 82a, 84a, 86a of the material section 34a. The overall width L1 in the transverse direction 38 of an unfolded front and rear material section attached to the main part 20 is 220 mm in the transverse direction 38. The width L2 of the segment 80b adjoining the main part 20 is approximately 70 mm. The width L3 of the central segment 82b and the width L4 of the central segment 84b is in each case approximately 40 mm, and the width L5 of the outer segment 86b comprising the edge region 37 is approximately 70 mm. The width of the region in which the material section 34a, 34b is attached overlappingly to the main part 20 is in each case approximately 25 mm to 30 mm. The length L6 of the material sections in the front section is 230 mm, the length L7 of the material sections in the back section is 300 mm.

In incontinence articles 9 in the sizes S (Small) and M (Medium), the overall width L1 in the transverse direction 38 of an unfolded front and rear material section is 140 mm to 180 mm. The width L2 of the segment 80b adjoining the main part 20 is 20 mm to 85 mm. The width L3 of the central segment 82b and the width L4 of the central segment 84b is in each case 20 mm to 45 mm, and the width L5 of the outer segment 86b comprising the edge region 37 is 50 mm to 60 mm. In the sizes L (Large) and XL (Extra Large), the overall width L1 is 200 mm to 265 mm, the width L2 is 45 mm to 125 mm, the width L3 and the width L4 are in each case 35 mm to 60 mm, and the width L5 is 55 mm to 85 mm.

Figure 4A:
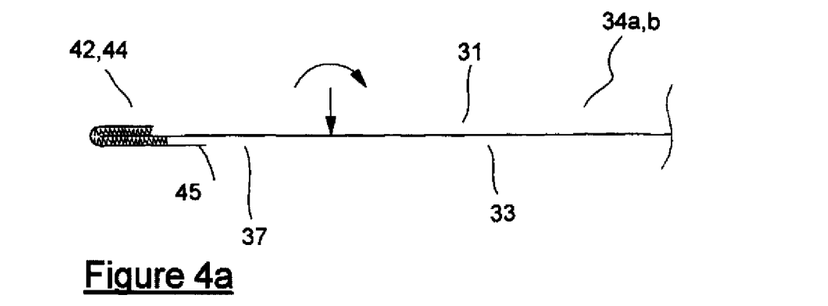
FIG. 4a shows a sectional view of a rear material section prior to folding onto itself and the step of the first folding onto itself
Figure 4B:
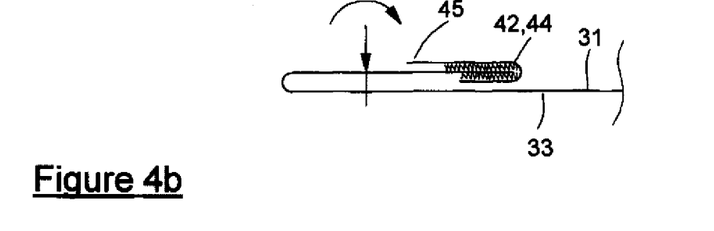
FIG. 4b shows a sectional view of a rear material section after the first folding onto itself and the step of the second folding onto itself
Figure 4C:
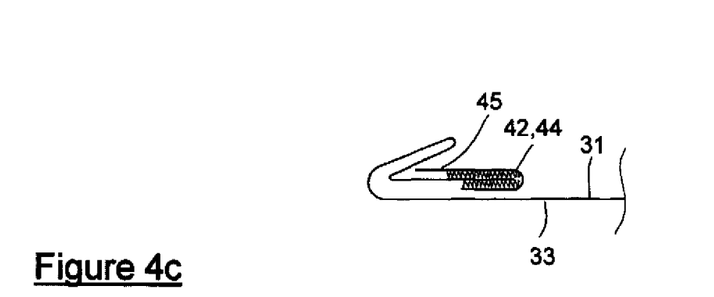
FIG. 4c shows a sectional view of a rear material section after the first and second folding onto itself

FIGS. 4a, 4b and 4c illustrate the folding of the material sections 34a, 34b onto themselves, with an outside 31 being first folded onto an outside 31 (FIG. 4a) to form a first folded arrangement (FIG. 4b). This now double-layered arrangement is folded again, now with an inside 33 coming to lie on an inside 33 (FIG. 4c).

The invention claimed is:

1. An absorbent incontinence article comprising:
a main part comprising an absorbent body and having a front section, a back section, and a crotch section arranged in a longitudinal direction of the incontinence article between the front and the back sections and positioned between the legs of a user;
rear material sections attached to respective lateral edge sections of the back section; and
front material sections attached to respective lateral edge sections of the front section, said rear and front material sections extending in a transverse direction of the incontinence article beyond lateral longitudinal edges of the main part, and interconnecting the front section and the back section in an applied state of the article, and having an inside and an outside, wherein in the applied state, the inside faces the body and the outside faces away from the body,
wherein said rear material sections have an outer longitudinal edge section provided with a closing element comprising a closing element tape having a free fingerlift tab, said closing element being folded back onto the inside of the rear material sections prior to use,
wherein the rear material sections are folded onto themselves prior to use of the article along fold lines extending parallel to the longitudinal direction and defining inner segments, central segments and outer segments of the rear material sections, said inner segments being attached to the respective lateral edge section of the main part, said outer segments comprising the longitudinal edge section,
wherein the central segments are folded onto the inside of the outer segments so that the central segments fully cover the free fingerlift tab of the closing element tape, wherein the thus folded rear material sections are turned in inward along turning-in axes onto an inside of the back section of the main part to form a turned-in arrangement, said inside of the edge section in the turned-in arrangement being oriented facing away from the inside of the back section of the main part, wherein an outer lateral edge of the outer segment of the rear material section projects in the transverse direction beyond the central segments folded over said lateral edge by a defined extent.

2. The absorbent incontinence article of claim 1, wherein the closing element tape is covered over at least 25% and at most 90% of its extent in the transverse direction, by central segments.

3. The absorbent incontinence article of claim 1, wherein the central segments cover the closing element tape over at least 10 mm and at most 50 mm, in the transverse direction.

4. The absorbent incontinence article of claim 1, wherein the defined extent is at least 10% and at most 85%, of the width L5 of each outer segment.

5. The absorbent incontinence article of claim 1, wherein the defined extent by which the outer lateral edge projects in the transverse direction is at least 5 mm and at most 50 mm.

6. The absorbent incontinence article of claim 1, wherein the fold lines together with a further fold line divide the rear material sections into four respective segments, wherein respective widths of central ones of the four segments is smaller than a respective widths of outer ones of the four segments.

7. The absorbent incontinence article of claim 6, wherein the widths of the central segments are identical and/or a ratio of the widths of the central segments to the widths of the outer segments is between 1:1 and 1:2.5.

8. The absorbent incontinence article of claim 1, wherein a gripping region is provided on a longitudinal edge section of each of the rear material sections.

9. The absorbent incontinence article of claim 1, wherein the rear material sections that are folded onto themselves in the longitudinal direction are turned in along the turning-in axes onto an inside of the back section so that the rear material sections come to lie at a small distance from one another or abut one another or overlap one another at least regionally.

10. The absorbent incontinence article of claim 1, wherein the front material sections are folded onto themselves prior to use of the folded-together article along the fold lines extending parallel to the longitudinal direction.

11. The absorbent incontinence article of claim 1, wherein the closing element tape is covered over at least 40% and at most 75% of its extent in the transverse direction by central segments.

12. The absorbent incontinence article of claim 1, wherein the central segments cover the closing element tape over at least 20 mm and at most 40 mm in the transverse direction.

13. The absorbent incontinence article of claim 1, wherein the defined extent is at least 40% and at most 60%, of the width L5 of each outer segment.

14. The absorbent incontinence article of claim 1, wherein the defined extent by which the outer lateral edge projects in the transverse direction is at least 24 mm and at most 36 mm.

15. An absorbent incontinence article comprising:
a main part comprising an absorbent body and having a front section, a back section, and a crotch section arranged in a longitudinal direction of the incontinence article between the front and the back sections and positioned between the legs of a user;
rear material sections attached to respective lateral edge sections of the back section; and
front material sections attached to respective lateral edge sections of the front section, said rear and front material sections extending in a transverse direction of the incontinence article beyond lateral longitudinal edges of the main part, and interconnecting the front section and the back section in an applied state of the article, and having an inside and an outside, wherein in the applied state, the inside faces the body and the outside faces away from the body,
wherein said rear material sections have an outer longitudinal edge section provided with a closing element comprising a closing element tape having a free fingerlift tab, said closing element being folded back onto the inside of the rear material sections prior to use,
wherein the rear material sections are folded onto themselves prior to use of the article along fold lines extending parallel to the longitudinal direction and defining inner segments, central segments and outer segments of the rear material sections, said inner segments being attached to the respective lateral edge section of the main part, said outer segments comprising the longitudinal edge section,
wherein the central segments are folded onto the inside of the outer segments so that the central segments fully cover the free fingerlift tab of the closing element tape, wherein the thus folded rear material sections are turned in inward along turning-in axes onto an inside of the back section of the main part to form a turned-in arrangement, said inside of the edge section in the turned-in arrangement being oriented facing away from the inside of the back section of the main part,
wherein an outer lateral edge of the outer segment of the rear material section projects in the transverse direction beyond the central segments folded over said lateral edge by a defined extent, and
wherein the fold lines divide each of the front material sections into four respective segments, wherein the front material sections are folded onto themselves prior to use of the folded-together article along the fold lines, and wherein respective widths of central ones of the four segments is smaller than respective widths of outer ones of the segments.

16. A method for manufacturing a folded incontinence article, comprising:
providing an absorbent incontinence which comprises
a main part comprising an absorbent body and having a front section, a back section, and a crotch section arranged in a longitudinal direction of the incontinence article between the front and the back sections and positioned between the legs of a user;
rear material sections attached to respective lateral edge sections of the back section; and
front material sections attached to respective lateral edge sections of the front section, said rear and front material sections extending in a transverse direction of the incontinence article beyond lateral longitudinal edges of the main part, and interconnecting the front section and the back section in an applied state of the article, and having an inside and an outside, wherein in the applied state, the inside faces the body and the outside faces away from the body,
wherein said rear material sections have an outer longitudinal edge section provided with a closing element comprising a closing element tape having a free fingerlift tab, said closing element being folded back onto the inside of the rear material sections prior to use;
folding the rear material sections onto themselves parallel to the longitudinal axis thereby forming a double-layered arrangement;
folding the double-layered arrangement onto itself parallel to the longitudinal axis, so that the free fingerlift tab of the closing element tape is fully covered by the central segments, thereby forming an at least regionally four-layered arrangement; wherein the rear material sections are folded onto themselves; and
turning the rear material sections in, inward along the turning-in axes onto an inside of the back section of the main part, so that the inside of the longitudinal edge section of the rear material sections is oriented facing away from the inside of the back section of the main part.

17. The method of claim 16, wherein the folding steps are performed in a production machine and wherein the incontinence articles are conveyed in the production machine parallel to the longitudinal direction at a web speed of more than 200 m/min.

18. The method of claim 16, further comprising folding the incontinence article inward onto itself at least once.

19. The method of claim 16, further comprising folding the incontinence article inward onto itself twice.

20. The method of claim 16, further comprising folding the incontinence article inward onto itself at least once along fold lines extending in the transverse direction.

21. The method of claim 16, further comprising folding the incontinence article inward onto itself twice so that the front section is first folded onto an inside of the main part and subsequently the back section is folded onto an outside of the front section.

22. The method of claim 16, wherein the incontinence articles are conveyed in the production machine parallel to the longitudinal direction at more than 300 m/min.

\* \* \* \* \*